US006274153B1

(12) United States Patent
Bruechert et al.

(10) Patent No.: US 6,274,153 B1
(45) Date of Patent: Aug. 14, 2001

(54) STRUCTURED COSMETIC MATERIAL COMPRISING κ-CARRAGHEEN WHICH FORMS A THREE-DIMENSIONAL NETWORK

(75) Inventors: Werner Bruechert, Oberasbach; Willy Weiss, Altdorf; Michael Healy, Nuremberg, all of (DE)

(73) Assignee: Schwan-Stabilo Cosmetics GmbH & Co., Heroldsberg (DE)

( * ) Notice: Subject to any disclaimer, the term of this patent is extended or adjusted under 35 U.S.C. 154(b) by 0 days.

(21) Appl. No.: 09/702,580

(22) Filed: Oct. 31, 2000

(30) Foreign Application Priority Data

Nov. 5, 1999 (DE) ................................ 199 53 336

(51) Int. Cl.⁷ ......................... A61K 6/00; A61K 7/021; A61K 7/027; A61K 7/42; A61K 7/32
(52) U.S. Cl. ......................... 424/401; 424/488; 424/64; 424/63; 424/DIG. 5; 424/195.17; 424/59; 514/844
(58) Field of Search ..................... 424/DIG. 5, DIG. 32, 424/400, 484, 488, 489, 499, 63, 64, 65, 78.03, 78.05, 401, 195.17, 59; 514/844

(56) References Cited

U.S. PATENT DOCUMENTS

| 5,658,580 | 8/1997 | Mausner ........................ 424/401 |
| 5,801,240 | * 9/1998 | Rideout et al. ............... 536/128 |
| 5,902,591 | * 5/1999 | Herstein ........................ 424/401 |

FOREIGN PATENT DOCUMENTS

| 3783741 | 5/1993 | (DE) . |
| 0203211 | 12/1986 | (EP) . |
| 0923931 | 6/1999 | (EP) . |
| WO 95/31967 | 11/1995 | (WO) . |
| WO 97/17053 | 5/1997 | (WO) . |
| WO 99/63951 | 12/1999 | (WO) . |

* cited by examiner

*Primary Examiner*—Diana Dudash
*Assistant Examiner*—Clinton Ostrup
(74) *Attorney, Agent, or Firm*—Bachman & LaPointe, P.C.

(57) ABSTRACT

A structured cosmetic material which includes water, a fat component, an o/w emulsifier, a w/o emulsifier, a polysaccharide such as κ-carragheen forming a three-dimensional network, and optionally conventional components.

11 Claims, No Drawings

STRUCTURED COSMETIC MATERIAL COMPRISING κ-CARRAGHEEN WHICH FORMS A THREE-DIMENSIONAL NETWORK

BACKGROUND OF THE INVENTION

The present invention concerns a structured cosmetic material and a process for the production thereof and use thereof.

The field of cosmetics, in particular decorative cosmetics, frequently involves the use of structured materials which are spread over or rubbed into the skin or mucous membrane and which are intended to remain there for a prolonged period of time. Materials of that kind are used for example in the form of cream, gel, compressed powder or in stick form. The use of sticks is popular for decorative cosmetics, in particular for eyes and lips, for example in the form of lipsticks, eyebrow pencils, kohl eye pencils or eye-shadow pencils. For that purpose of use the material must be sufficiently firm to be able to form stick portions, but on the other hand it should be such that it can be well and properly applied and is to stay on for a long time without being sticky. Furthermore as far as possible it should also be water-resistant and should not irritate the skin. If the stick used is a rotational stick having a rotary mechanism into which the stick portion is fitted and projects unsupportedly therefrom, the material must also be of adequate strength.

There are already numerous compositions for the production of sticks. Thus for example stick materials are described and produced, which contain volatile solvents which evaporate at body temperature. The volatile solvent provides that the material can be easily applied. After evaporation of the solvent after application to the skin, the material has good adhesion to the skin. It will be noted however that in recent times the use of volatile solvents is undesirable for environmental reasons. It would therefore be desirable to provide a material which manages with water as a solvent.

Aqueous stick materials have already been described, which occur in the form of aqueous gels. For example WO97/17055 describes gel sticks which can contain a high proportion of water, but which must also contain at least 20% by weight of a water-soluble or water-dispersible gel-forming agent. Upon application, the high proportion of gel-forming agent gives a sticky, unpleasant feel.

DE 196 432 37 describes sticks which can have a water content of between 30 and 85% by weight. Here the stick material is produced in the form of a firm water/oil (w/o) emulsion. In those materials the aqueous phase is used to incorporate into a stick substances which are soluble in water but not in the fat phase. The products which are described here are however still not satisfactory as they are not stable at elevated temperatures and separate into the phases.

Therefore it is the object of the present invention to provide a cosmetic material which occurs in structured form, which can be processed to form sticks, which has good mechanical properties, which can absorb a large amount of water, which is extremely stable in respect of temperature, which is stable over a wide pH-range and is stable in terms of storage without change at up to about 60° C. and which can be applied at up to 45° C. The invention further seeks to provide that the cosmetic material is wipe-resistant but can easily be uniformly applied and is to give a good feel on the skin. In addition it is to afford materials enjoying good strong colours for decorative cosmetics.

SUMMARY OF THE INVENTION

The foregoing object is attained by a structured cosmetic material which includes water, a fat component, an o/w emulsifier, a w/o emulsifier, a polysaccharide forming a three-dimensional network, and optionally conventional components.

It was found that, in accordance with the invention, it is possible to obtain an extremely temperature-stable, structured material if a dispersion comprising a water component and a fat component is combined with a combination of a w/o emulsifier and an o/w emulsifier and a polysaccharide which forms a three-dimensional network is added to that composition. The material according to the invention involves a dispersion type which has a continuous aqueous phase but which essentially does not exhibit any emulsion features. The addition of the specific polysaccharide produces a firm structure so that the material can be shaped, for example can be processed to make it into stick portions which can be used both in stick tubes and also in relation to the rotary mechanism of rotational sticks.

DETAILED DESCRIPTION

The material according to the invention includes water and a fat component as its main components. Water can be contained in the material in a proportion of between 30 and 85% by weight, preferably between 40 and 75% by weight and particularly preferably between 50 and 65% by weight, in each case with respect to the weight of the overall composition. A part of the water evaporates upon application to the skin and gives a pleasantly cooling feel on the skin.

The fat component of the cosmetic material according to the invention comprises oil and/or wax components. All waxes and oils which are conventionally used in the cosmetics field are suitable here. The choice in that respect depends on the purpose for which the cosmetic material is to be used. Natural and synthetic oils, for example vegetable oils and ester oils or silicone oils are suitable as oil components. Examples that may be mentioned for oil components are jojoba oils, castor oil, olive oil and vegetable triglyceride oils. Examples of ester oils are jojobates, myristylmyristate, isopropylmyristate and isopropylpalmitate. Both volatile and also non-volatile silicone oils can be used as the silicone oils. For sticks of harder texture such as for example eyebrow sticks or pencils and kohl eye pencils, paraffin, ceresin, ozocerite and microcrystalline waxes are preferably used. The waxes which are conventional in cosmetics are considered as the wax component. An example is polyethylene wax.

An essential aspect of the invention is the combination of o/w emulsifier and w/o emulsifier. The emulsifiers adopted in themselves are not critical and it is possible to use the emulsifiers which are conventionally employed in cosmetic materials. It is however essential that, out of each of the two classes, the material contains at least one representative thereof. The ratio between the two emulsifiers is preferably between 1:5 and 5:1, particularly preferably between 1:2 and 2:1. The o/w emulsifiers are preferably long-chain esters of polyvalent alcohols, for example long-chain esters of glycerine and sucrose, wherein the alcohol components preferably have between 14 and 26 carbon atoms, in particular between 18 and 24 carbon atoms.

The w/o emulsifiers are preferably ethylene oxide derivatives such as PEG-30-dipolyhydroxystearate or emulsifiers from the group of ceteareths, as well as higher alcohols, for example those with between 20 and 40 C-atoms. Examples are polyoxyethylene-20; polyoxyethylene-30; ceteareth-20; ceteareth-30; polyoxyethylene-24-glycerine monostearate and polyoxyethylene-10-oleyl cetyl alcohol or mixtures thereof.

A further constituent, which is essential to the invention, of the cosmetic material according to the invention is a polysaccharide which can form a three-dimensional network. The man skilled in the art can establish which polysaccharides are suitable here, by carrying out a small number of experiments, by checking what kind of gel structure is formed by a polysaccharide being considered. Only those which produce three dimensional structures are suitable for the composition according to the invention.

An example in this respect, which is particularly preferably used, is κ-carragheen. Carragheen, also referred to as carrageenan, is obtained from red algae, in particular those of the families Gigartinaceae or Solieriaceae and are complex mixtures of various polysaccharides. Fractional precipitation makes it possible to obtain various components of the carragheen, which can be organised into classes; one of these is κ-carragheen.

It was surprisingly found that polysaccharides which can form a three-dimensional structure such as κ-carragheen can impart a firm structure to the dispersion according to the invention while polysaccharides which form two-dimensional networks, for example other kinds of carragheen such as iota-carragheen or lambda-carragheen only produce pasty products which are easy to spread and which cannot be processed to form structured materials, in particular not sticks. A polysaccharides, as defined hereinbefore, results in combination with the o/w emulsifier and the w/o emulsifier in the dispersion in a structure which remains stable even at relatively high temperatures.

In accordance with the invention κ-carragheen is preferably used as the polysaccharide. The polysaccharide is preferably used in a proportion of between 0.05 and 18% by weight. A smaller amount no longer affords the advantageous properties while an amount exceeding 18% by weight does not give any further advantages but can produce an unpleasantly sticky feel. The polysaccharide is particularly preferably used in an amount of between 0.1 and 10% by weight and in particularly in an amount of between 0.3 and 4% by weight.

The features which are essential to the invention are therefore the use of a combination of o/w emulsifier and w/o emulsifier and the addition of polysaccharide, in particular κ-carragheen. It is only when using that combination for a dispersion containing water and fat components, that the result obtained is a structured material with the stated desirable properties.

The cosmetic material according to the invention may also contain conventional ingredients. It usually contains dyestuffs or colorants, colouring lakes, pigments and/or pearl lustre agents in order to impart the desired appearance to the material. In accordance with the invention all colouring agents of the kind and in the amount which are conventional in cosmetics and which are permitted by the respective statutory regulations of the individual countries concerned can be used. As the cosmetic material contains a proportion of water, water-soluble and water-dispersible dyestuffs can advantageously be used.

It is also usual for thickening agents or fillers to be added to cosmetic materials in order to adjust their consistency and influence the structure. All thickening agents and fillers which are usual here are suitable. For example it is possible to use kaolin, talc and modified starches. The cosmetic material according to the invention may also contain agents for improving the structure and for affording better administration to the skin. Examples that may be mentioned in this respect are boron nitrite, lauroyl lysine, modified kinds of mica, Nylon 12 and PMMA. Those additives are used in the amount which is conventional for cosmetic materials. Anti-oxidants and anti-microbial agents may also be included in the cosmetic material according to the invention in the amounts which are conventional in themselves, to enhance stability. The cosmetic materials may further contain conventional stabilisers, for example kester wax or $C_{20}$–$C_{40}$-alcohols. A moistening agent, for example a polyvalent alcohol such as sorbitol, glycerine or propylene glycol can also be added in the conventional amount.

Further subject-matter of the invention is a process for the production of a firm cosmetic material, characterised in that the fat constituents and the emulsifiers are heated until they are highly fluid and possibly pigments and fillers are added, separately therefrom the polysaccharide is dissolved in water, the fat and the aqueous phases are combined at a temperature in the range of between 50 and 100° C., homogenisation, air removal and cooling are effected and possibly thermally labile constituents are added and then storage is effected.

As the cosmetic material according to the invention has both a water component and also a fat component, all water-soluble or water-dispersible and fat-soluble additives, which are usual in cosmetics, can be used without any problems. It will be noted however that the use of heat-labile raw materials, that is to say materials which cannot withstand temperatures of more than 60° C., is less desirable. As the production of the cosmetic materials according to the invention is more appropriately effected at a temperature in the range of between 50 and 100° C., it is preferable to use those raw materials which can withstand the temperatures in that range. If heat-labile materials are used, they have to be incorporated at the end of the production process.

The firm cosmetic material according to the invention is produced by a procedure whereby the fat constituents are heated until they are fluid and then the fat-soluble or fat-dispersible constituents are added and possibly homogenised. The polysaccharide is then dissolved in the aqueous phase in a hot condition. Water-soluble and water-dispersible ingredients can possibly be added. The fat phase and the aqueous phase are then combined at a temperature in the range of between 50 and 100° C., preferably between 60 and 80° C., in particular between 70 and 75° C., homogenised and air removed therefrom. Temperature-labile substances, for example anti-oxidants, preserving agents and care substances can then be added. If materials of that kind are added, the cosmetic material is briefly homogenised once again. The cosmetic material is then cooled down and can be stored in that form. It is stable over several months without phase separation occurring.

To produce sticks, the cosmetic material, without cooling, can be poured into prepared tubes or shaped to form stick portions which are then fitted into a tube or the rotary mechanism of a rotational stick. Stick portions of a diameter of between 2 and 12 mm are preferably formed.

The cosmetic material according to the invention is particularly preferably used to produce lipsticks, lip liners, eye-shadow pencils, eye-liners, eyebrow pencils, sun protection sticks and deodorant or anti-perspirant sticks. Depending on the respective purpose of use involved, the respectively necessary further constituents can be added to the cosmetic material, that is to say in the case of decorative cosmetics dyestuffs and lustre pigments, in the case of sun protection sticks sun blockers with a sun protection factor and in the case of deodorant sticks or antiperspirant sticks, perfumes and perspiration-inhibiting agents. The man skilled in the art is aware of the respective appropriate ingredients so that they do not need to be further described herein.

Set forth hereinafter are also some embodiments for further describing the invention. In this respect the raw materials are identified by the usual INCI names.

EXAMPLE 1

The composition for an eye-liner according to the invention is set out hereinafter. The constituents are identified by the usual INCI names and the amounts are specified in percent in each case in relation to the overall composition.

| | |
|---|---|
| Aqua | 60.000 |
| Colorants | 12.000 |
| Sorbitol solution | 7.000 |
| Cetearyl behenate | 6.500 |
| Cyclomethicone | 6.000 |
| PVP eicosene copolymer | 3.500 |
| Ceteareth-16 | 2.000 |
| PEG-30 dipolyhydroxystearate | 2.000 |
| Chondrus Crispus (κ-carragheen) | 1.000 |
| | 100.000 |

The fat constituents were heated together with the emulsifiers to between 70 and 75° C. and the colorants and fillers added. The carragheen was dissolved in water in a hot condition. The two phases were then combined, homogenised and air removed therefrom. The material was shaped to form a stick portion and fitted into a tube. The eye-liner stick obtained can be easily applied and an applied line adheres well to the skin.

EXAMPLE 2

The composition for an eyebrow pencil according to the invention is set out hereinafter. The constituents are identified by the usual INCI names and the amounts are specified in percent in each case in relation to the overall composition.

| | |
|---|---|
| Aqua | 65.000 |
| Colorants | 10.000 |
| Cyclomethicone | 6.000 |
| Ceteareth-16 | 2.000 |
| PEG-30 dipolyhydroxystearate | 2.000 |
| Chondrus Crispus (κ-carragheen) | 1.000 |
| Glycerine | 4.000 |
| Polyethylene | 7.000 |
| PVP/hexadecene copolymer | 3.000 |
| | 100.000 |

Production of the stick was implemented as described in Example 1. The stick obtained can be applied well and was stable even when stored for a prolonged period of time.

EXAMPLE 3

The composition for an kohl eye pencil according to the invention is set out hereinafter. The constituents are identified by the usual INCI names and the amounts are specified in percent in each case in relation to the overall composition.

| | |
|---|---|
| Aqua | 62.500 |
| Colorants | 12.000 |
| PVP eicosene copolymer | 2.500 |
| Chondrus Crispus (κ-carragheen) | 1.000 |
| Isostearyl alcohol | 6.000 |
| Propylene glycol | 6.000 |
| Sucrose tetrastearate triacetate | 3.500 |
| PVP/hexadecene copolymer | 1.500 |
| $C_{20}$–$C_{40}$ alcohols | 5.000 |
| | 100.000 |

Production of the stick was implemented as described in Example 1. The stick obtained can be applied well and was felt pleasant.

EXAMPLE 4

The composition for an lip liner according to the invention is set out hereinafter. The constituents are identified by the usual INCI names and the amounts are specified in percent in each case in relation to the overall composition.

| | |
|---|---|
| Aqua | 65.000 |
| Colorants | 12.000 |
| Sorbitol solution | 6.000 |
| Chondrus Crispus (κ-carragheen) | 1.000 |
| Sucrose tribehenate | 4.000 |
| Sucrose polyinoleate | 2.000 |
| Dimethicone | 2.000 |
| $C_{20}$–$C_{40}$ alcohols | 6.000 |
| Jojoba oil | 2.000 |
| | 100.000 |

Production of the stick was implemented as described in Example 1. Lines could be well drawn with the stick obtained and they enjoy good adhesion to the skin.

EXAMPLE 5

The composition for an lip liner according to the invention is set out hereinafter. The constituents are identified by the usual INCI names and the amounts are specified in percent in each case in relation to the overall composition.

| | |
|---|---|
| Aqua | 65.000 |
| Colorants | 12.000 |
| Cyclomethicone | 6.000 |
| PEG-30 dipolyhydroxystearate | 2.000 |
| Chondrus Crispus (κ-carragheen) | 1.000 |
| Glycerine | 5.000 |
| Sucrose tribehenate | 4.000 |
| $C_{20}$–$C_{40}$ alcohols | 2.000 |
| Jojoba oil | 3.000 |
| | 100.000 |

Production of the stick was implemented as described in Example 1. The stick portion produced with the material was sufficiently firm that it could be fitted into a rotary mechanism and could be extended by turning without breaking off.

What is claimed is:

1. A three dimensional structured cosmetic material comprising between 30 and 85% by weight of water, between 2 and 15% by weight of an o/w emulsifier and a w/o emulsifier, between 0.05 and 18% by weight k-carragheen which forms a three dimensional network, balance essentially a fat phase.

2. A cosmetic material according to claim 1 wherein the fat phase is selected from the group consisting of oil and wax components.

3. A cosmetic material according to claim 1 wherein the fat phase forms between 10 and 25% by weight of the cosmetic material.

4. A cosmetic material according to claim 1 wherein the o/w emulsifier and the w/o emulsifier are present in a ratio by weight of between 1:5 and 5:1.

5. A cosmetic material according to claim 1 wherein the κ-carragheen is present in a proportion of between 0.1 and 10% by weight.

6. A cosmetic material according to claim 1 wherein the κ-carragheen is present in a proportion of between 0.3 and 4% by weight.

7. A cosmetic material according to claim 1 wherein the cosmetic material further comprises anti-oxidants, preserving agents, fillers, dyestuffs and pearl luster pigments.

8. A process for the production of a firm cosmetic material comprising a three dimensional structured cosmetic material comprising water, a fat phase, an o/w emulsifier, a w/o emulsifier and a κ-carragheen which forms a three dimensional network comprising the steps of heating the fat constituents and the emulsifiers until they are highly fluid, dissolving the κ-carragheen in water combining the heated fat and the κ-carragheen agueous phases at a temperature in the range of between 50 and 100° C. to form a mixture, and thereafter homogenizing and cooling the mixture.

9. A process according to claim 8 wherein the mixture is processed to form stick portions.

10. A process according to claim 8 or claim 9 wherein the mixture is cast to form a stick portion and same is fitted into a tube of a rotational stick.

11. A cosmetic material according to claim 1 selected from the group consisting essentially of lipsticks, lip liners, eye-shadow pencils, eye-liners, eyebrow pencils, sun protection sticks, deodorant sticks and anti-perspirant sticks.

* * * * *